United States Patent [19]
Bath

[11] Patent Number: 6,083,192
[45] Date of Patent: *Jul. 4, 2000

[54] PULSED ULTRASOUND METHOD FOR FRAGMENTING/EMULSIFYING AND REMOVING CATARACTOUS LENSES

[76] Inventor: Patricia E. Bath, 4554 Circle View Blvd., Suite 2001, Los Angeles, Calif. 90043

[*] Notice: This patent issued on a continued prosecution application filed under 37 CFR 1.53(d), and is subject to the twenty year patent term provisions of 35 U.S.C. 154(a)(2).

[21] Appl. No.: 08/800,495

[22] Filed: Feb. 14, 1997

Related U.S. Application Data

[63] Continuation of application No. 08/474,773, Jun. 7, 1995, abandoned, which is a continuation-in-part of application No. 07/717,794, Jun. 19, 1991, Pat. No. 5,871,498, which is a continuation of application No. 07/159,931, Feb. 24, 1988, abandoned, which is a division of application No. 06/943,098, Dec. 18, 1986, Pat. No. 4,744,360.

[51] Int. Cl.[7] .................................................. A61B 17/36
[52] U.S. Cl. ................................ 604/22; 604/27; 606/1
[58] Field of Search ................... 606/1, 2, 3–19; 604/20–32

[56] References Cited

U.S. PATENT DOCUMENTS

| | | | |
|---|---|---|---|
| 3,352,303 | 11/1967 | Delaney | 604/22 |
| 3,433,226 | 3/1969 | Boyd | 604/22 |
| 3,589,363 | 6/1971 | Banko et al. | 604/22 |
| 3,971,383 | 7/1976 | Krasnov . | |
| 3,982,541 | 9/1976 | L'Esperance, Jr. . | |
| 4,538,608 | 9/1985 | L'Esperance, Jr. . | |
| 4,583,539 | 4/1986 | Karlin et al. | 606/14 |
| 4,686,979 | 8/1987 | Gruen et al. . | |
| 4,729,373 | 3/1988 | Peyman | 606/4 |
| 4,744,360 | 5/1988 | Bath | 606/6 |
| 5,324,282 | 6/1994 | Dodick | 606/2 |
| 5,334,183 | 8/1994 | Wuchinich | 606/16 |

OTHER PUBLICATIONS

"Similarities and Differences between Fiber Acoustics and Fiber Optics" by Jen; 1985 Ultrasonics Symposium.
C. Davis Belcher III, "The Future", *Ophthalmic Laser Therapy*, vol. 2, No. 4, 1987.
C. Davis Belcher III, "Phacoablation", *Ophthalmic Laser Therapy*, vol. 3, No. 1, 1988.
Gailitis et al., "Comparison of Laser Phacovaporization . . . ", '78/SPIE vol. 1744, *Ophthalmic Technologies II* (1992).

*Primary Examiner*—David M. Shay

[57] ABSTRACT

A method and apparatus for removing cataracts in which a flexible line preferably is inserted through an incision into the anterior chamber until its end is adjacent the cataract. Ultrasonic energy, preferably up to 100 Mhz, is coupled to the cataract by an optical fiber in the line. An irrigation sleeve provided about the optical fiber and an aspiration sleeve extending partially around the irrigation sleeve conduct irrigating liquid to and remove the fragmented/emulsified material from the anterior chamber and form with the fiber the flexible line.

6 Claims, 2 Drawing Sheets

PULSED ULTRASOUND METHOD FOR FRAGMENTING/EMULSIFYING AND REMOVING CATARACTOUS LENSES

This application is a continuation, of application Serial No. 08/474,773, filed Jun. 7, 1995, now abandoned which is a C-I-P of Ser. No. 07/717,794, filed Jun. 19, 1991; now U.S. Pat. No. 5,871,498, which is a continuation of Ser. No. 07/159,931, filed Feb. 24, 1988, now abandoned, which is a divisional of Ser. No. 06/943,098, filed Dec. 18, 1986, now U.S. Pat. No. 4,744,360.

FIELD OF THE INVENTION

The present invention relates to a method and apparatus for coupling ultrasound (energy) to an optical fiber combined with irrigation/aspiration for therapeutic purposes directed to and within a cataractous lens.

BACKGROUND OF THE INVENTION

For many years optical fibers have been utilized in the medical industry to transmit light (laser energy) to targets for diagnostic as well as therapeutic purposes. Every eye is divided into an anterior and posterior chamber separated by a normally transparent lens which focuses light onto the retina at the back of the posterior chamber. When the lens becomes cloudy for any of a variety of reasons sight is impaired and the cloudy lens must be removed. Following removal of the lens, an inter ocular lens (IOL) implant can be placed in the posterior chamber or thick glasses or contact lenses used to focus the light.

A number of techniques are now in use for this common surgical procedure. An incision can be made in the eye and a sharp instrument inserted to cut and then aspirate by vacuum the cloudy cataract tissue. More recently, a small incision-typically 3 mm-can be made in the eye surface and a metal tipped ultrasonic probe inserted to a position adjacent the lens. The ultrasonic energy then disintegrates the lens material which can likewise be removed by aspiration.

Laser radiation is now used widely in various surgical techniques particularly those involving the eye. For example, the patent to Krasnov, U.S. Pat. No. 3,971,382, describes a technique in which laser radiation is focused onto the anterior capsule of the lens to form a hole through which the cataract substance can be drawn from the lens capsule.

Optical fibers are also commonly used for medical and other applications to transmit coherent radiation from a laser to some location in the body where material is to be coagulated or disintegrated. U.S. patent application Ser. No. 702,569, filed Feb. 19, 1985, describes a micro instrument with an optical fiber. The optical fiber can be inserted into the eye for the removal of abnormal tissue such as tumors. Radiation with a wavelength between 200 and 400 nm is said to be appropriate. However, a problem with laser based systems is that there is the potential for explosions in the eye.

As above mentioned, it is known to use ultrasonic energy to disintegrate cataracts in the eye. This technique is known as phacoemulsification. In such a technique, a metal tip valve is utilized at high frequencies. In such a technique, a metal tip vibrates at high frequencies. The phacoemulsification technique is limited because a metal tip associated therewith becomes very hot at high frequencies, thereby potentially damaging the eye. Due to the heat associated with the high frequency output, the current practice has been to avoid utilizing this technique with hard cataracts.

Accordingly, what is needed is a cataract removal system that does not have the heat problems associated with the phacoemulsification process and also is not susceptible to the explosions generated by laser based systems. The present invention addresses such a need.

SUMMARY OF THE INVENTION

The present invention relates to a method and apparatus in which ultrasound energy is transmitted by a flexible line containing an optical fiber is inserted through a limbel incision, preferably 1 mm or less, in the eye surface and then through a 1 mm or less anterior capsulofomy into the lens nucleus. The optical fiber is then positioned within the crystalline lens.

Ultrasound energy delivered to the optical fiber fragments the crystalline material into extremely small particles less than 0.1 mm in diameter. These fragmented particles and cortex can then be irrigated and aspirated from the capsular bag, which is left intact, except for the 1 mm anterior capsulatomy, via an aspiration sleeve which is formed about and extending along the optical fiber. At the same time irrigating liquid is supplied via an irrigation sleeve likewise formed about and extending along the optical fiber.

Since the particles produced by the disintegration are so small, the device can be made to be extremely small and therefore, the incision likewise can be made much smaller. Utilizing an optical fiber further permits the energy to be more efficiently and effectively focused onto the lens to be removed.

The present invention employs an optical fiber which allows high frequency probe output without the high temperatures associated with conventional ultrasound procedures for removing cataracts. In summary, the present invention exploits the advantage of utilizing an optical fibers to precisely deliver units of energy to loci within the lens. However, the unique anatomy of the lens lends itself to mechanical-nonlinear disruption, i.e., the optical fiber ultrasound delivery system of the present invention.

DETAILED DESCRIPTION OF THE INVENTION

The present invention is an improvement in the removal of a cataract lens. The following description is presented to enable one of ordinary skill in the art to make and use the invention and is provided in the context of a patent application and its requirements. Various modifications to the preferred embodiment and the generic principles and features described herein will be readily apparent to those skilled in the art.

Applicant has observed that the optical fiber when conducting laser energy vibrates. It was determined that some of the vibrations emanated from the lens itself as a result of laser-lens tissue interaction. At the instant of optical breakdown in the target zone acoustic shock waves are created. These acoustic shock waves may be generated purposefully by configuration of laser parameters to maximize the photoacoustic component of the optical breakdown or the shock waves may simply occur as a minor component of the process. Significantly, it was this observation of shock waves travelling along the optical fiber in the opposite direction of the laser energy that led to the hypothesis that shock waves could be purposely propagated down an optical fiber for therapeutic purposes.

Heretofore, in the medical industry, the ability of optical fibers to transmit sound has only been exploited in the area of diagnostics. U.S. Pat. No. 5,217,018 dated Jun. 8, 1993 entitled "Acoustic Transmission Through Cladded Core Waveguide", for example, teaches such a use of an optical fiber. The above-identified patent discloses: "This invention constitutes a major step forward in the continually evolving field of medical imaging."

Accordingly, Applicant has discovered that an optical fiber in combination with an ultrasound generator can be utilized for therapeutic purposes to fragment/emulsify cataractous lenses through the use of an ultrasound generator. In a preferred embodiment, the ultrasound generator includes a transducer located on a piezoelectric head to which an optical fiber bundle is linked. In a preferred embodiment, the ultrasound generator will operate up to 100 Mhz.

Figure 1:
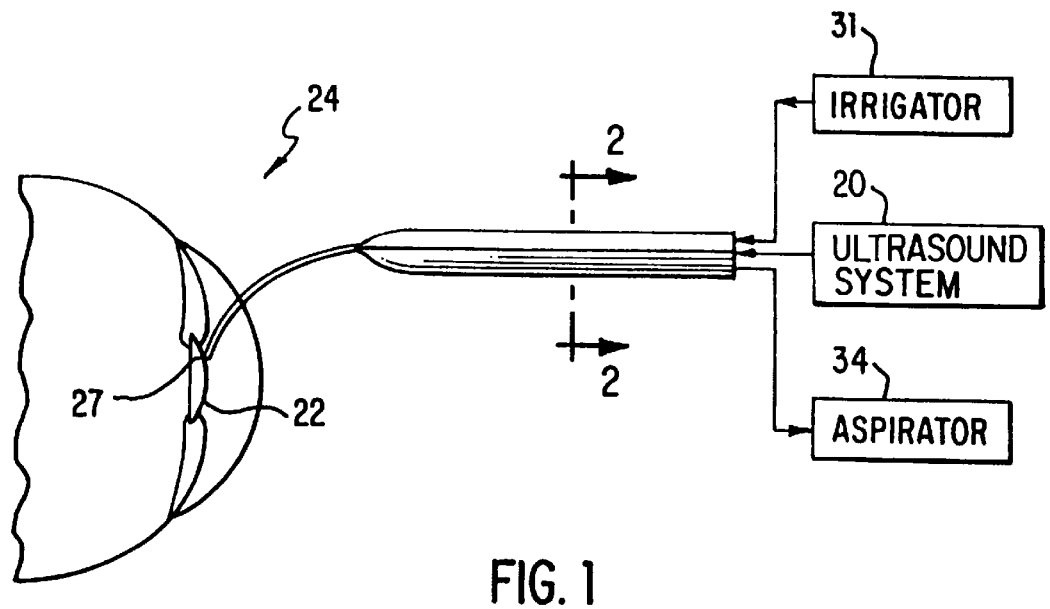
FIG. 1 shows a schematic view of the present invention being used for disintegrating a cataract lens.
Figure 2:
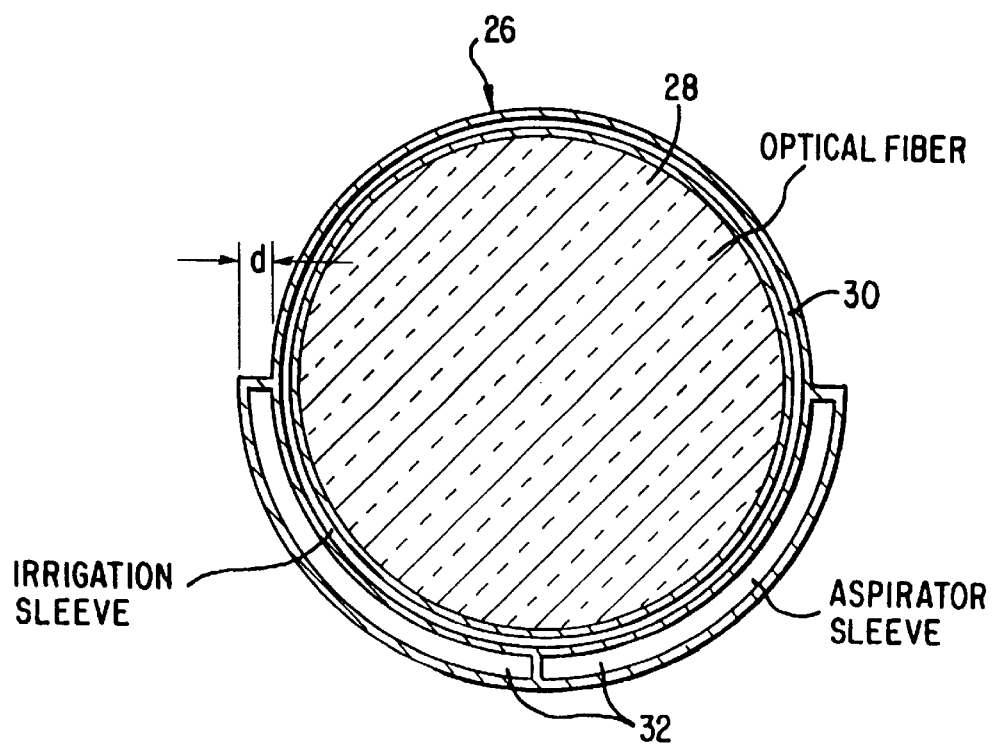
FIG. 2 shows a cross-section of the flexible line of FIG. 1 along the lines 2—2.
Figure 1A:
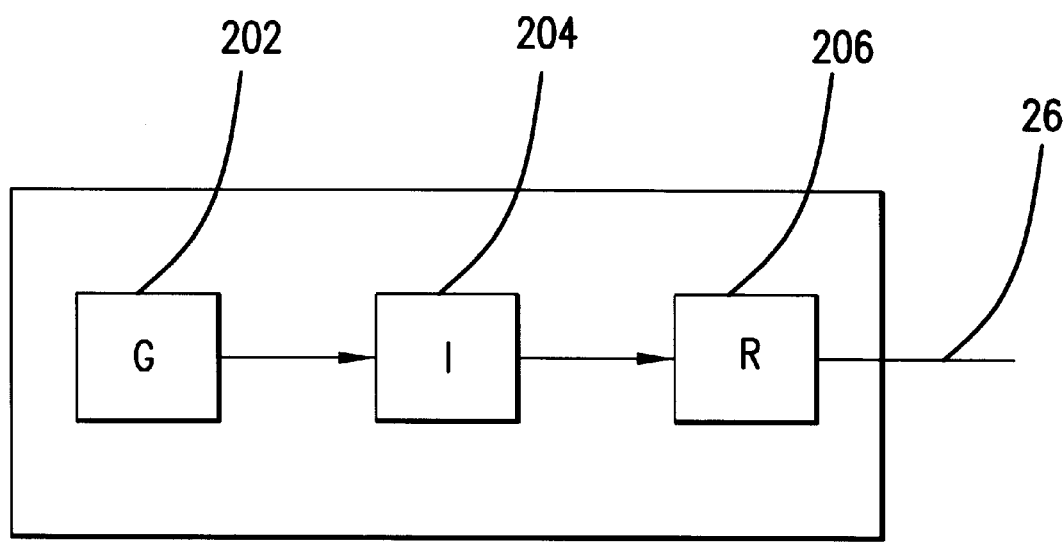
FIG. 1A shows a schematic view of the ultrasonic source coupled to the flexible line.

To more particularly describe the present invention, reference is now made to FIGS. 1, 1A and 2 which illustrate a preferred embodiment of the present invention. First, a flexible line 26 is introduced into the interior of the lens nucleus through a 1 mm limbel incision and a 1 mm anterior capsulotomy. Ultrasonic energy from a suitable ultrasonic energy source 20 at a suitable energy level is coupled to the interior aspect of a cataract lens 22 in a human or animal eye 24 by a flexible line 26 until the desired amount of fragmentation/emulsification occurs.

Referring to FIG. 1A, a typical ultrasonic energy source would comprise an ultrasound generator 202 which is coupled to an ultrasound integrator and focusing member 204 which in turn is coupled to an ultrasound transducer 206. The ultrasound generator 202 in a preferred embodiment would include a piezoelectric head which is coupled to the optical fiber.

As can be best seen in FIG. 2, flexible line 26 is formed of a conventional optical fiber 28 suitable for medical applications, for example, quartz silica. The formed of the conventional optical fiber, is then directed successively to the inferior, central and superior areas of the lens nucleus and ultrasonic energy is again performed at each area. An irrigation sleeve 30 surrounds the optical fiber and is connected to a suitable irrigation device 31 for supplying irrigating liquid to the eye during surgery at a suitable pressure. Aspiration sleeve 32 extends partially around the irrigation sleeve to form a flexible tube formed of the line 26 (in the form of an optical fiber) the irrigation sleeve and the aspiration sleeve. The aspiration sleeve 32 is coupled to a conventional aspirator 34 for removing by an appropriate suction the minute particles of cataract tissues which are produced in response to incidence of the sonic fragmentation/emulsification.

Since the particles are so small, the width d of the aspiration sleeve can be 0.3 mm or less. The ultrasonic energy fiber can be made to no more than 600 microns in diameter and the aspiration sleeve similarly no more than 0.1 mm so that the entire flexible tube can be made of a diameter no greater than 1 mm, permitting the size of the incisions to be minimized.

Although the present invention has been described in accordance with the embodiments shown in the figures, one of ordinary skill in the art recognizes there could be variations to the embodiments and those variations would be within the spirit and scope of the present invention. Accordingly, many modifications may be made by one of ordinary skills in the art without departing from the spirit and scope of present invention, the scope of which is defined solely by the appended claims.

What is claimed is:

1. A method of removing cataracts from an eye comprising the steps of:

making an incision into an anterior chamber and on an anterior surface of a capsular bag; including the steps of inserting into the anterior chamber and the capsular bag a line including at least a line fabricated of fiber-optic material, the line having a proximal end driven by ultrasound energy and a distal end in contact with the cataractous lens, the line having an irrigation sleeve extending at least partially about and along the fiber-optic line, and an aspiration sleeve extending at least partially about and along the irrigation sleeve;

coupling ultrasonic energy to the proximal end of the fiber-optic line so that the line vibrates percussively at frequencies sufficient to fragment the cataractous lens into extremely small particles, applying fluids through the irrigation sleeve to entrain the extremely small particles, and applying suction through the aspiration sleeve to effectively remove said the extremely small particles.

2. The method of claim 1, further including pulses of ultrasonic energy frequencies coupled to the fiber-optic line are sufficiently high, to effect cavitation within the cataractous lens.

3. The method of claim 1, including the step of reducing heat generated by ultrasonic vibration of the line is effected substantially by surrounding the fiber optic line in whole or in part by the irrigation and aspiration sleeve conducting the fluids.

4. The method of claim 1, further including the steps of entraining the extremely small particles by irrigating, and aspirating the extremely small entrained particles.

5. The method of claim 1, further including the step of reducing heat generated by ultrasonic vibration of the line by surrounding the fiber optic line with irrigant.

6. The method of claim 5, further including the steps of entraining the extremely small particles by irrigating, and aspirating the extremely small entrained particles.

* * * * *